(12) United States Patent
Hahn et al.

(10) Patent No.: US 6,512,946 B1
(45) Date of Patent: Jan. 28, 2003

(54) METHOD OF DETECTING CARDIAC INTERVAL SIGNALS IN CARDIOLOGIC DEVICES

(75) Inventors: Andreas Hahn, Berlin (DE); Andreas Kucher, Schwedt (DE)

(73) Assignee: Biotronik Mess und Therapiegerate GmbH & Co. Ingenieurburo Berlin, Berlin (DE)

( * ) Notice: Subject to any disclaimer, the term of this patent is extended or adjusted under 35 U.S.C. 154(b) by 232 days.

(21) Appl. No.: 09/599,219

(22) Filed: Jun. 22, 2000

(30) Foreign Application Priority Data

Jun. 23, 1999  (DE) .......................... 199 28 656

(51) Int. Cl.$^7$ ................................ A61B 5/04
(52) U.S. Cl. .......................... 600/519; 607/27
(58) Field of Search .................. 600/516, 519, 600/521, 509; 607/9, 27

(56) References Cited

U.S. PATENT DOCUMENTS 4,549,551 A   10/1985  Dyck et al.
5,776,168 A   7/1998   Gunderson
6,129,745 A * 10/2000  Sun .............................. 607/27

FOREIGN PATENT DOCUMENTS

DE   2331551   8/1982

\* cited by examiner

*Primary Examiner*—George R. Evanisko
*Assistant Examiner*—Roderick Bradford
(74) *Attorney, Agent, or Firm*—Browdy and Neimark

(57) ABSTRACT

A method of detecting cardiac interval signals in cardiologic devices comprises the following method steps:

time-resolved detection of cardiac events which are representative of the cardiac intervals;

determination of the respective cardiac interval values between two successive cardiac events;

statistical evaluation of a certain number of successive cardiac interval values; and individual comparison of the certain number of cardiac interval values with each other such that individual cardiac interval values which deviate significantly from cardiac interval values that occur there-before and there-after are recognized as faulty measurements and corrected.

5 Claims, 7 Drawing Sheets

1. $\overline{PP}$ = (480+480+480+480)/4 = 480  =  1. $\overline{RR}$ = (480+480+480+480)/4 = 480
2. $\overline{PP}$ = (480+480+480+__220__)/4 = 415  <  2. $\overline{RR}$ = (480+480+480+480)/4 = 480
3. $\overline{PP}$ = (480+480+__220__+__260__)/4 = 360  <  3. $\overline{RR}$ = (480+480+960+480)/4 = 480
4. $\overline{PP}$ = (480+__220__+__260__+480)/4 = 360  <  4. $\overline{RR}$ = (480+480+480+480)/4 = 480
5. $\overline{PP}$ = (__220__+__260__+480+480)/4 = 360  <  5. $\overline{RR}$ = (480+480+480+480)/4 = 480
6. $\overline{PP}$ = (__260__+480+480+480)/4 = 425  <  6. $\overline{RR}$ = (480+480+480+480)/4 = 480
7. $\overline{PP}$ = (480+480+480+480)/4 = 480  =  7. $\overline{RR}$ = (480+480+480+480)/4 = 480

METHOD OF DETECTING CARDIAC INTERVAL SIGNALS IN CARDIOLOGIC DEVICES

BACKGROUND OF THE INVENTION

1. Field of the Invention

The invention relates to a method of detecting cardiac interval signals in cardiologic devices, in particular of detecting tachycardiac arrhythmias, comprising the following method steps: time-resolved detection of cardiac events which are representative of the cardiac interval; determination of the respective cardiac interval between two successive cardiac events; statistical evaluation of a certain number of successive cardiac interval values.

2. Background Art

From relevant technical devices, for instance cardiac pacemakers used to combat tachycardiac arrhythmias, it is known to detect cardiac events of the monitored heart by special detection methods, to subject the measuring results obtained therefrom to corresponding evaluation criteria, and, based thereon, to determine corresponding therapy deliveries to the monitored heart, for instance in the form of electric pulses, by the aid of suitable algorithms. Cardiac events to be used are for example the stimulus signals that occur during atrial and ventricular contraction of the heart, which are representative of the cardiac interval—the time interval between two contractions of the heart.

Atrial and ventricular heart rates or intervals and the comparison thereof can be used among others as a criterion for the existence of tachycardiac arrhythmias.

For evaluation implementation in prior art cardiologic devices, it has been known to make use of the cardiac events which are representative of the cardiac intervals and are detected in time resolution, in order to determine the respective heart interval between two of these successive cardiac events. A certain number of successive heart interval values are then statistically evaluated so as to suppress, to a certain degree, faulty measurements. For instance, a so-called "x out of y control" is carried out, in which defined events are used as a basis for the determination of suitable therapy deliveries in the cardiologic device only when they have occurred x times out of y detections.

In connection with the detection of tachycardiac arrhythmias, sliding averaging is standard for the statistical evaluation, in which a certain number of successive cardiac interval values are subjected to continuous averaging. When atrial and ventricular events are used in practice for heart interval determination, the continuously detected atrial and ventricular averages of the cardiac interval values are compared with each other, significant deviations of these averages from each other and defined behaviors of successive averages suggesting to certain arrhythmias. Based on the detection specified above, corresponding therapy deliveries to the monitored heart are then detected in accordance with given algorithms in the control of the cardiologic device. These sequences, a very abstract idea of which has been given above, are put into practice by correspondingly programmed algorithms in the microprocessor based control systems of today's cardiologic devices.

Of course, faulty measurements may occur during the detection of cardiac events. For example, so-called "undersensing" or "oversensing" can be found in the detection of atrial and ventricular events. "Undersensing" is the faulty non-detection of atrial or ventricular events that have really taken place. "Oversensing" is a faulty measurement, in which a pulse is detected without any corresponding atrial or ventricular event having taken place.

In cardiac interval determination, single atrial or ventricular "undersensing" has the effect of doubling the heart interval value determined therefrom. In a statistic evaluation in the form of averaging of for example four successive heart intervals, the faulty measurement enters four times in succession into sliding averaging. Consequently, the real heart interval is not correctly determined four times in succession, which—in particular in the case of repetition—may give rise to inadequate therapy delivery by the cardiologic device, entraining corresponding risks for the patient.

SUMMARY OF THE INVENTION

It is the object of the invention to improve the method of detecting cardiac interval signals such that individual faulty measurements are recognizable and correctable in particular with a view to the statistical evaluation of successive cardiac interval values.

This object is attained in that along with the statistical evaluation of the certain number of successive cardiac interval values, an individual comparison of this certain number of cardiac interval values with one another takes place in such a way that individual cardiac interval values, which significantly deviate from cardiac interval values that occur there-before or there-after, are recognized as faulty measurements and correspondingly corrected.

The method according to the invention profits from the knowledge that in the detection of cardiac interval signals, faulty measurements will occur as so-called "outliers", which are characteristic individual events. Such an individual event becomes recognizable by a continuous comparison of successively detected heart intervals in particular in a retrospective view and, based on the storage capacities of the microprocessor based control systems of nowadays cardiologic devices and implants, it can be employed for a corresponding correction of the cardiac events from which to determine therapy. Preferably in the case of superimposed statistical evaluation and correction of the detected heart interval values, the heart intervals which have been evaluated statistically can be corrected subsequently upon recognition of a faulty measurement.

Statistic evaluation on the basis of sliding averaging preferably makes use of at least four successive cardiac interval determinations. Preferably, the individual comparison of the heart intervals with one another for the recognition of faulty measurements then takes place, based on a number of cardiac intervals which is identical with the number of cardiac interval determinations used for averaging.

Further preferred embodiments of the method according to the invention involve special method steps dealing with faulty events in the case of the mentioned "undersensing" and "oversensing" during the detection of atrial or ventricular events. Details of this will become apparent from the ensuing description of an exemplary embodiment of a method according to the invention, taken in conjunction with the drawing.

BRIEF DESCRIPTION OF THE DRAWING

FIG. 3 is a table illustrating the continuous comparison between mean heart intervals of atrial and ventricular events in the case of atrial "undersensing";

FIGS. 4 and 5 are diagrams analogous to FIGS. 2 and 3 in the case of ventricular "undersensing";

DESCRIPTION OF THE PREFERRED EMBODIMENT

Figure 1:
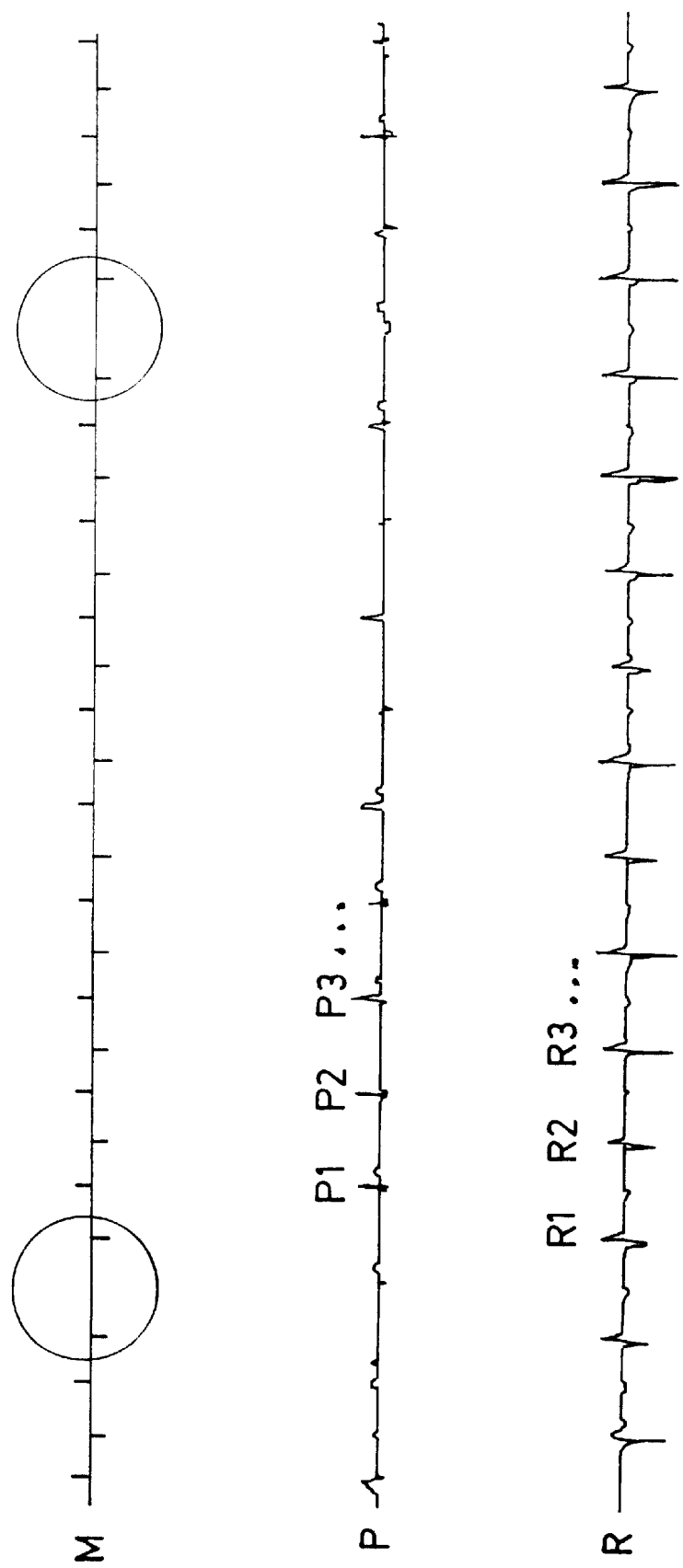
FIG. 1 is a measuring diagram based on the time-resolved detection of atrial and ventricular events.

Proceeding from FIG. 1, the method of detection according to the invention is explained, based on an individual case of atrial "undersensing". The starting point is the electrocardiogram of the heart (details of which are seen in FIG. 1) as recorded by an anti-tachycardia implant for the combat of cardiac arrhythmias. Cardiac events used therein are the atrial stimulus signals on the one hand, which are represented by the so-called P wave of the electrocardiogram (line P in FIG. 1). The time intervals between the individual P waves P1, P2, P3 . . . determine the atrial heart intervals of the monitored heart.

Further, the R waves R1, R2, R3 . . . seen in line R of FIG. 1 are detected as a cardiac event, representing the ventricular stimulation of the monitored heart. The intervals between the individual R waves R1, R2, R3 . . . are representative of the ventricular heart intervals of the monitored heart. Finally, line M of FIG. 1 illustrates the so-called "marker" of the anti-tachycardia implant, which reflects the conversion of the real signals of the P and R waves in the implant into triggered base signals of the occurrence of the respective P and R wave P1, P2, P3 . . . , R1, R2, R3 . . .

The portions of line M which are marked by a circle show that a P wave has not been detected, owing to a faulty measurement, and that consequently, no corresponding atrial event is recognized by the implant. A faulty measurement has taken place in the form of atrial "undersensing".

Figure 2:
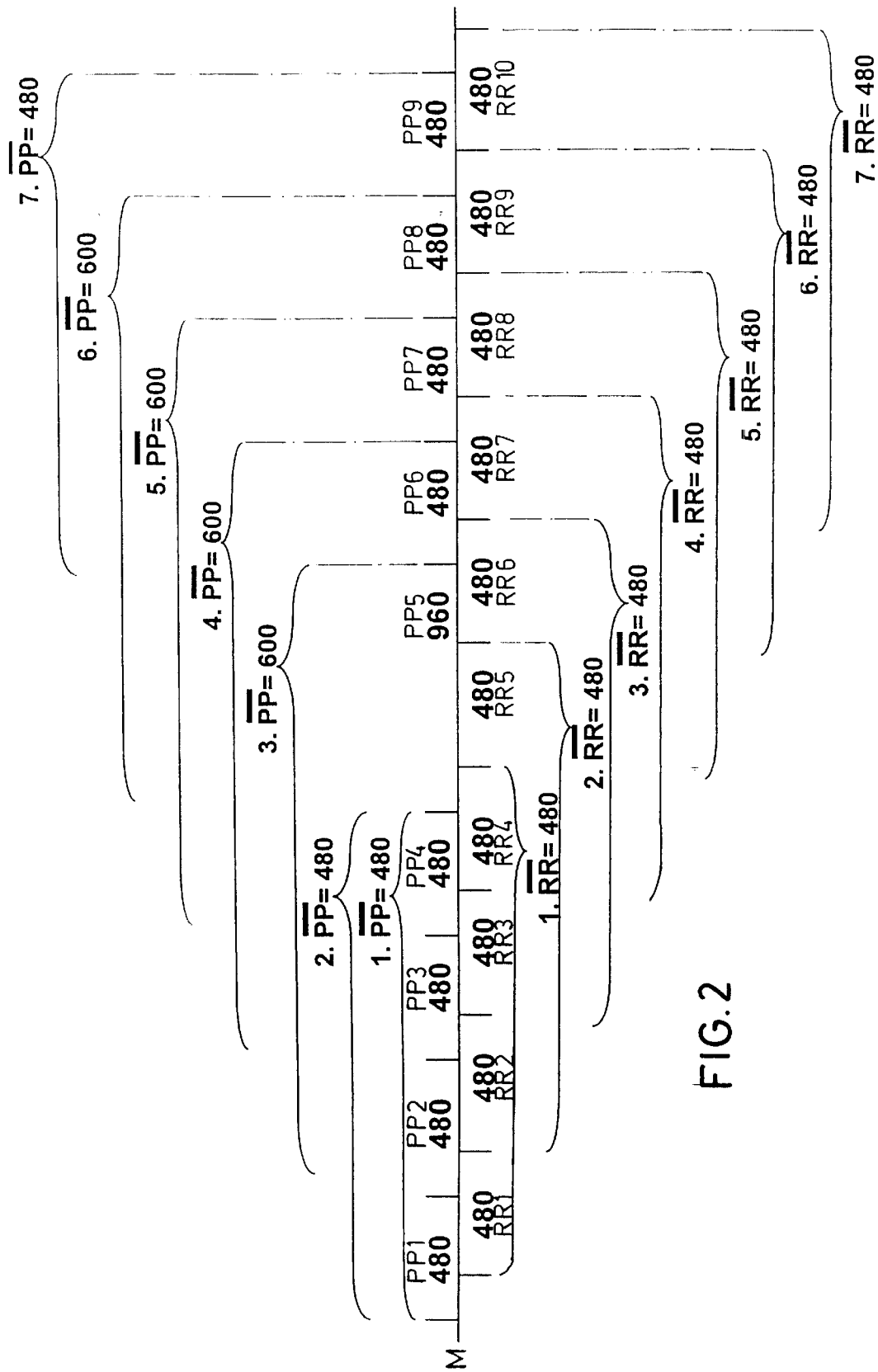
FIG. 2 is a graph for the illustration of continuous averaging in the statistical evaluation of successive atrial and ventricular cardiac intervals without correction according to the invention.
Figure 3:
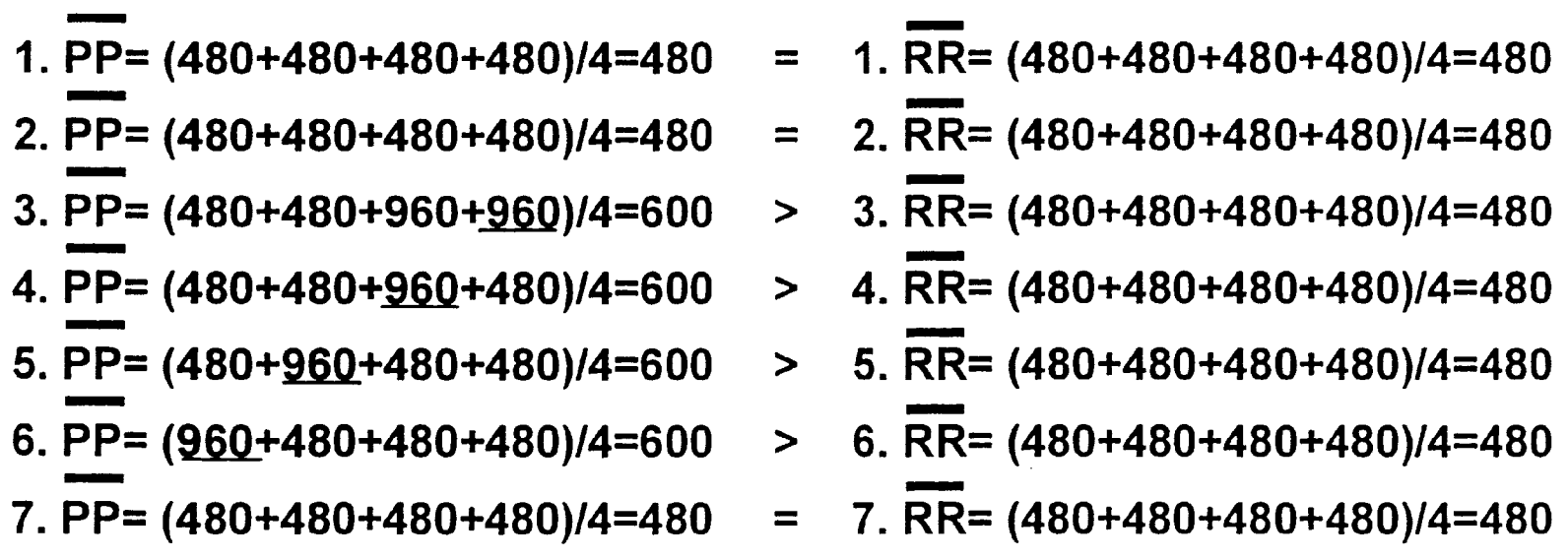

The further statistical evaluation of the atrial and ventricular events and the influence of the above-mentioned faulty measurement is explained in conjunction with FIGS. 2 and 3. Successive cardiac interval values between two successive atrial or ventricular events are determined from the marker. As seen from line M of FIG. 2, the cardiac intervals between the atrial P waves are in each case 480 ms with the exception of the portion of faulty measurement, where an interval of 960 ms (2×480 ms) results.

The R waves, which are displaced in time as compared to the P waves and in which no faulty measurement has taken place, show heart intervals of 480 ms.

For statistical evaluation, continuous averaging takes place over four heart intervals PP1, PP2, PP3, PP4, then PP2, PP3, PP4, PP5, then PP3, PP4, PP5, PP6 etc. By analogy, sliding averaging is performed for the ventricular events, covering in each case four ventricular heart intervals RR1, RR2, RR3, RR4, then RR2, RR3, RR4, RR5 etc. Corresponding mean values 1.$\overline{PP}$, 2.$\overline{PP}$, 3.$\overline{PP}$ . . . and 1.$\overline{RR}$, 2.$\overline{RR}$, 3.$\overline{RR}$ etc. are formed therefrom.

As seen in FIG. 3, the faulty measurement of the atrial interval PP5 in the amount of 960 ms in the case of four successive mean values, namely 3.$\overline{PP}$ to 6.$\overline{PP}$, gives an incorrect mean value of 600 ms. Since the mean value $\overline{PP}$ is in each case compared with the associated mean value $\overline{RR}$ of the ventricular event the comparisons 3.$\overline{PP}$/3.$\overline{RR}$ to 6.$\overline{PP}$/6.$\overline{RR}$ determine a mean atrial interval to mean ventricular interval ratio which does not correspond to reality. This faulty determination may lead to the erroneous assumption that there is a ventricularly conditioned tachycardia, because—as erroneously assumed—the heart beats faster ventricularly than it does atrially.

Along with the above statistical evaluation on the basis of sliding averaging of four successive intervals, the method according to the invention proceeds with an individual comparison of four successive cardiac interval values at a time. During the comparison 2.$\overline{PP}$/2.$\overline{RR}$, for instance, also the four atrial cardiac intervals PP1, PP2, PP3, PP4 are compared with one another. As they are equal, no error is recognized.

In the ensuing comparison 3.$\overline{PP}$/3.$\overline{RR}$, the atrial heart intervals PP2, PP3, PP4 and PP5 are compared with each other. PP5 is found to differ significantly from the preceding intervals PP2, PP3, PP4, namely by twice the value. A corresponding note is entered in the control program of the implant.

During the following comparison 4.$\overline{PP}$/4.$\overline{RR}$, the atrial heart intervals PP3, PP4, PP5, PP6 are compared with each other and it is found that the heart interval PP6 has returned to the original value of PP3, PP4. This is recognized as a criterion for the fact that PP5 must be a faulty measurement—i.e. an "outlier"—as a result of which the cardiac interval value PP5 is corrected. Correspondingly, the mean values 3.$\overline{PP}$, 4.$\overline{PP}$, 5.$\overline{PP}$ and 6.$\overline{PP}$ are corrected retrospectively to be 480 ms, the corresponding comparisons 3.$\overline{PP}$/3.$\overline{RR}$, 4.$\overline{PP}$/4.$\overline{RR}$ etc. are repeated and correspondingly re-evaluated. This process, which is not set out as such in FIGS. 2 and 3, results in that identical atrial and ventricular mean values are determined in the comparisons $\overline{PP}$/$\overline{RR}$, which leads to the amended evaluation, namely that there is no tachycardia.

The foregoing clearly shows that in the case of faulty non-detection of a cardiac event, such as atrial "undersensing", precisely one cardiac interval PP5 must deviate significantly from the cardiac intervals PP4, PP6 determined there-before and there-after, which leads to the recognition of a faulty measurement and corresponding correction of this value.

Figure 4:
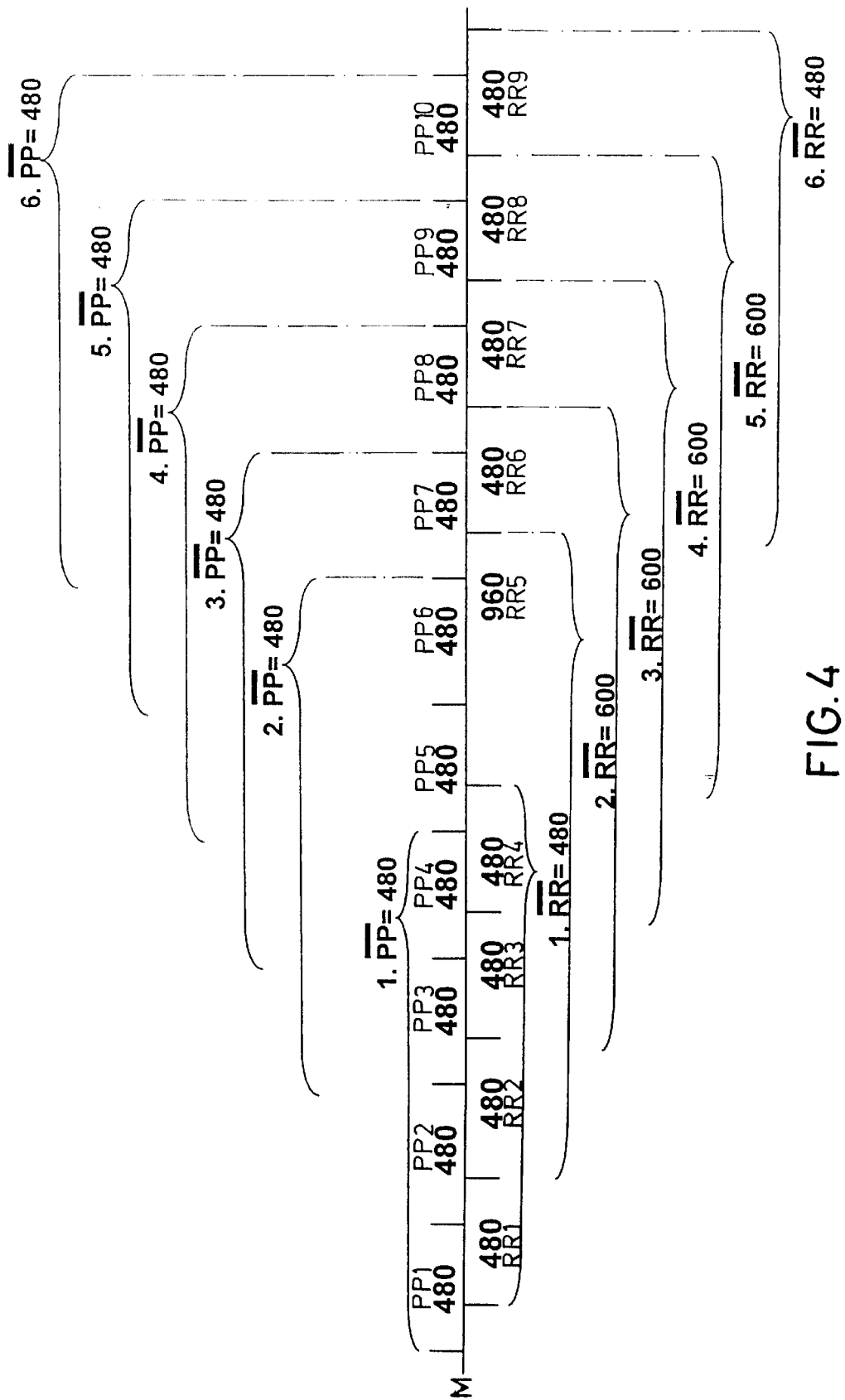
Figure 5:
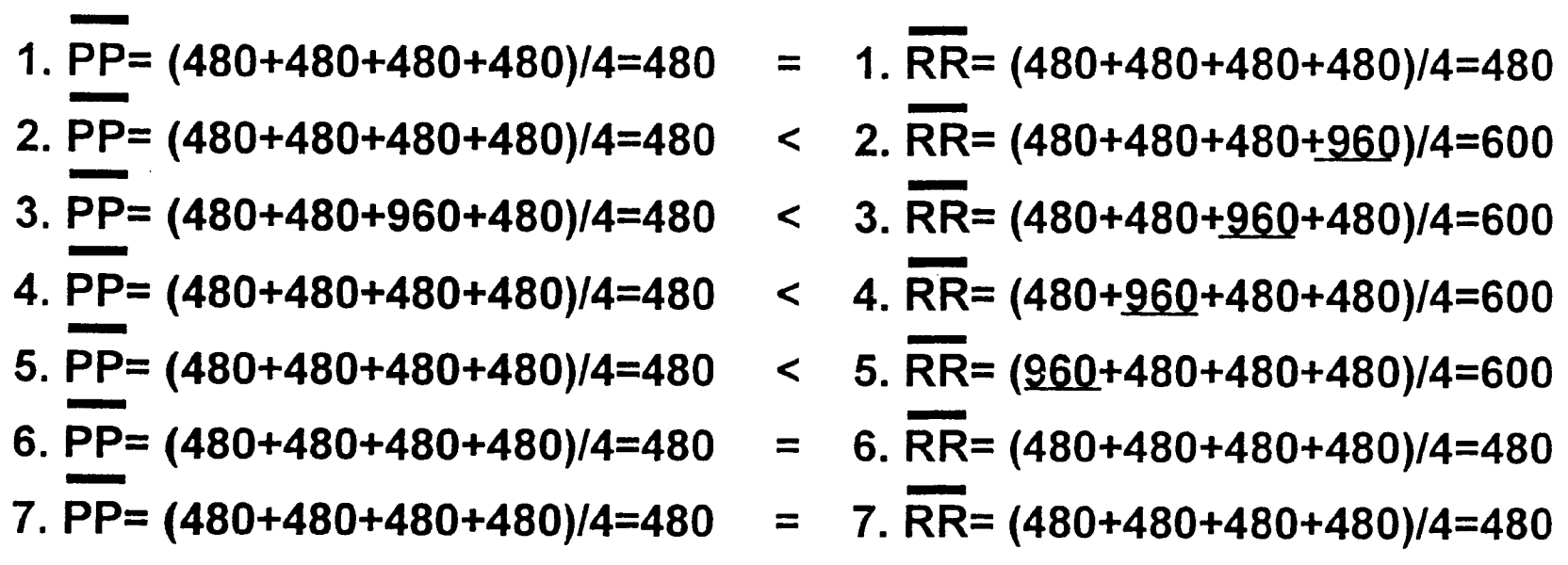

Sporadic ventricular "undersensing" and the correction thereof are explained, based on FIGS. 4 and 5. Since again use is made of the fundamental statistical methods of evaluation, namely sliding averaging of four successive heart interval values PP1, PP2, PP3, PP4 and RR1, RR2, RR3, RR4, respectively, there is no need of renewed explanation. It has to be mentioned that the cardiac interval value RR5 is erroneously determined to be 960 ms because of a faulty measurement in an R wave. As a result, four successive averaging processes 2.$\overline{RR}$ to 5.$\overline{RR}$ will determine the mean value incorrectly to be 600 ms. The comparisons 2.$\overline{PP}$/2.$\overline{RR}$ to 5.$\overline{PP}$/5.$\overline{RR}$ (see FIG. 5) wrongly evaluate that the ventricular cardiac interval is greater than the atrial cardiac interval. This is considered to be a criterion for the presence of atrial tachycardia.

In addition to the atrial cardiac interval values PP1, PP2 . . . , the method of correction according to the invention also subjects the ventricular cardiac intervals RR1, RR2 . . . to an individual comparison. During this comparison, the incorrect cardiac interval RR5 is recognized—as already explained on the basis of FIGS. 2 and 3 in conjunction with the P waves—and can be corrected to be 480 ms. Then the averaged cardiac interval values—as they are still incorrectly listed in FIG. 5—are also corrected retrospectively on the side of the R waves so that the mean values $2.\overline{RR}$ to $5.\overline{RR}$ are amended to be 480 ms. The comparisons $2.\overline{PP}/2.\overline{RR}$ to $5.\overline{PP}/5.\overline{RR}$ then performed result in the criterion that there are equal cardiac intervals on the atrial and ventricular side. Misinterpretation of the rhythms due to differing intervals is avoided, consequently the customary criterion of evaluation used for atrially and ventricularly equal cardiac intervals can be applied.

Figure 6:
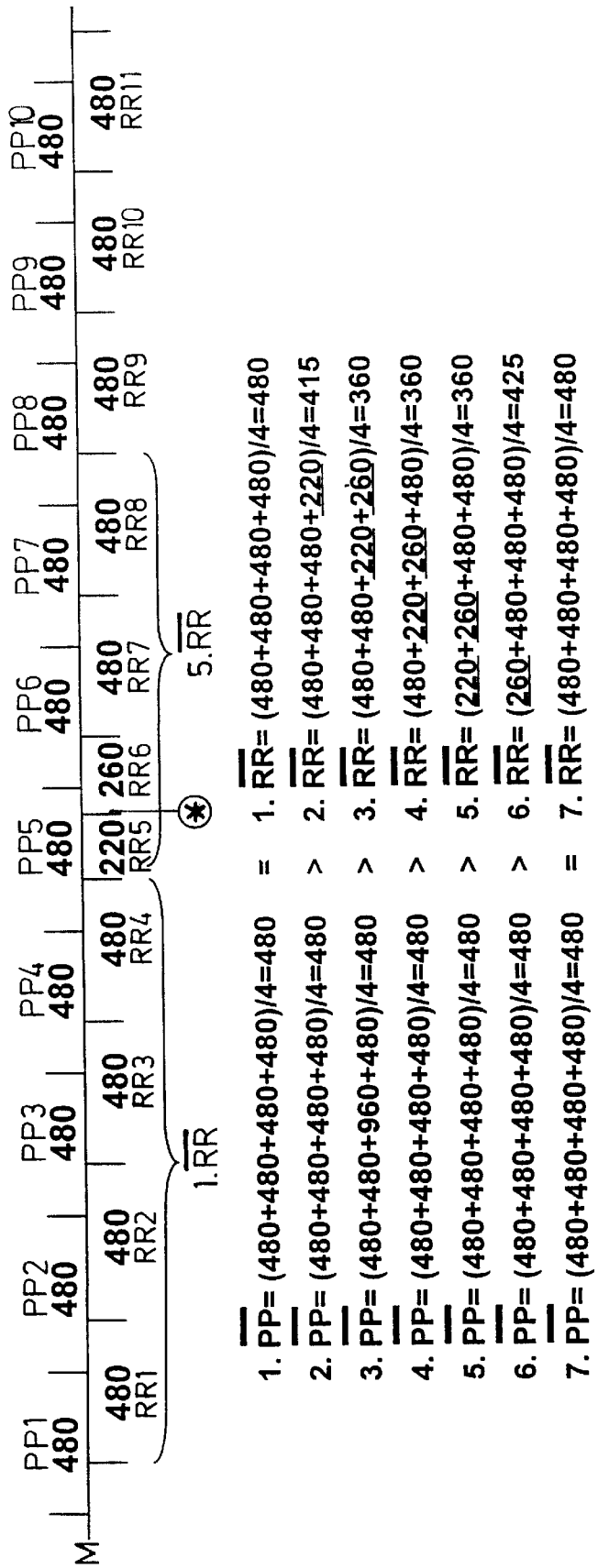
FIG. 6 is a combined illustration, by analogy to FIGS. 2 and 3, in the case of ventricular "oversensing"

FIG. 6 illustrates sporadic ventricular "oversensing" which manifests itself by the wave provided with an asterisk in the marker M and erroneously detected as an R wave. Due to this faulty measurement, the ventricular cardiac intervals RR5 and RR6 are incorrectly determined to be 220 and 260 ms, respectively. Sliding averaging will consequently give the incorrect ventricular interval averages $2.\overline{RR}$ to $6.\overline{RR}$. The correctly measured atrial cardiac intervals PP1, PP2 . . . lead to correct cardiac interval averages $1.\overline{PP}$, $2.\overline{PP}$ etc.

In the comparisons $2.\overline{PP}/2.\overline{RR}$ to $6.\overline{PP}/6.\overline{RR}$, an incorrect ratio is determined between RR5 and RR6 because of ventricular "oversensing", namely that $2.\overline{PP}$ to $6.\overline{PP}$ is in each case greater than $2.\overline{RR}$ to $6.\overline{RR}$. This leads to the erroneous assumption of the existence of ventricular tachycardia.

Based on the method according to the invention, the individual comparison of the cardiac intervals finds out that the values RR5 and RR6 are significantly smaller than RR4, but that RR7 is again equal to the original value RR4. The fact that precisely two successive cardiac intervals significantly undershoot the preceding or following values is used as a criterion for a faulty measurement and the two cardiac intervals RR5 and RR6 are subsequently corrected to constitute a single correct cardiac interval of a duration of 480 ms. In the manner already described this influences the averaged cardiac interval values $2.\overline{RR}$ to $6.\overline{RR}$ to the effect that each is corrected to be 480 ms. The subsequently re-evaluated comparisons $2.\overline{PP}/2.\overline{RR}$ to $6.\overline{PP}/6.\overline{RR}$ will give the result that the atrial and ventricular cardiac intervals are identical, i.e. that an otherwise customary criterion of evaluation can be applied.

Sporadic ventricular "oversensing" or an interposed ventricular extra systole (VES) are equally treated by the correction algorithm, although a VES is a real cardiac signal. i.e., a VES is likewise discriminated and remains unevaluated. This is a desired side effect, because there is no obligation of treatment of ventricular extra systoles and fulfilling any onset or stability criterion inadequately is thus precluded.

Figure 7:
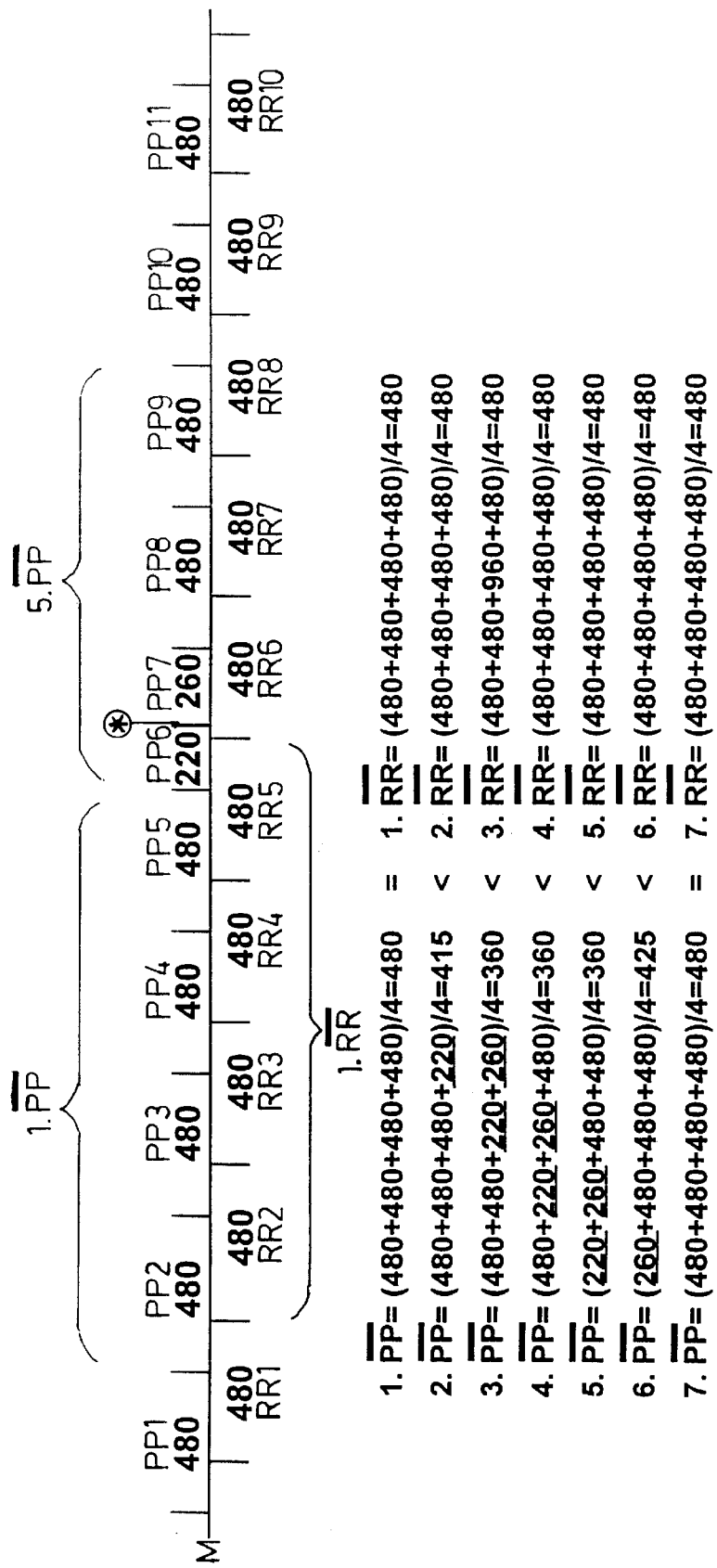
FIG. 7 is a combined illustration, by analogy to FIGS. 2 and 3, in the case of atrial "oversensing".

FIG. 7 is an illustration, by analogy to FIG. 6, of a faulty measurement due to atrial "oversensing". By reason of the above explanations with regard to ventricular "oversensing", this illustration is explanatory by itself and in order to avoid repetitions, reference is made to the explanations in connection with FIG. 6, which are directly applicable thereto.

What is claimed is:

1. A method of detecting cardiac interval signals in cardiologic devices, comprising the following method steps:

detecting cardiac events which are representative of a cardiac interval in time-solved manner, determining a respective cardiac interval value between two successive cardiac events;

statistically evaluating a predetermined number of successive cardiac interval values by slidingly averaging at least four successive cardiac interval values;

individually comparing, along with the statistical evaluation of the predetermined number of successive cardiac interval values, this predetermined number of cardiac interval values among one another for a number of cardiac interval values which is identical with the number of the cardiac interval values used for sliding averaging, recognizing individual, significant cardiac interval values, which deviate from cardiac interval values that occur there-before and there-after, as faulty measurements and correcting said faulty measurements.

2. A method according to claim 1, comprising a case of a superimposed statistical evaluation and correction of the detected cardiac interval values, the step of subsequently correcting the statistically evaluated cardiac interval values.

3. A method according to claim 1, wherein in a case of a faulty non-detection of a cardiac event, precisely one cardiac interval deviates significantly from cardiac interval values determined there-before and there-after and comprising the step of correcting this deviating value to correspond to these values.

4. A method according to claim 1, wherein in a case of a faulty detection of a cardiac event, precisely two successive cardiac interval values deviate significantly form the cardiac interval values determined before and after this pair of values and comprising the step of correcting said two successive cardiac interval values jointly to correspond to said values determined before and after.

5. A method according to claim 1, comprising the step of detecting one of an atrially conditioned P wave and a ventricularly conditioned R wave of an electrocardiogram of a monitored heart as cardiac events.

\* \* \* \* \*